(12) United States Patent
Blight et al.

(10) Patent No.: US 10,647,735 B2
(45) Date of Patent: May 12, 2020

(54) METAL COMPLEXES AND METHODS OF PREPARING THE SAME

(71) Applicant: University of New Brunswick, Fredericton (CA)

(72) Inventors: Barry A Blight, Fredericton (CA); Barbora Balónová, Fredericton (CA)

(73) Assignee: University of New Brunswick, Fredericton, NB (CA)

( * ) Notice: Subject to any disclaimer, the term of this patent is extended or adjusted under 35 U.S.C. 154(b) by 0 days.

(21) Appl. No.: 16/033,754

(22) Filed: Jul. 12, 2018

(65) Prior Publication Data
US 2020/0017535 A1    Jan. 16, 2020

(51) Int. Cl.
*C07D 235/30* (2006.01)
*C07D 471/04* (2006.01)
*C09K 11/06* (2006.01)
*C07F 15/00* (2006.01)

(52) U.S. Cl.
CPC ........ *C07F 15/0033* (2013.01); *C07D 235/30* (2013.01); *C07D 471/04* (2013.01); *C09K 11/06* (2013.01); *C09K 2211/1029* (2013.01); *C09K 2211/1044* (2013.01); *C09K 2211/1092* (2013.01); *C09K 2211/185* (2013.01)

(58) Field of Classification Search
CPC ... C07F 15/00; C07D 235/30; C07D 4712/04; C09K 11/06
See application file for complete search history.

(56) References Cited

U.S. PATENT DOCUMENTS

| | | |
|---|---|---|
| 6,670,645 B2 | 12/2003 | Grushin et al. |
| 7,338,722 B2 | 3/2008 | Thompson et al. |
| 7,691,292 B2 | 4/2010 | Chichak et al. |
| 8,557,402 B2 | 10/2013 | Thompson et al. |
| 8,808,878 B2 | 8/2014 | Hou et al. |
| 2008/0161568 A1 | 7/2008 | Chi et al. |

OTHER PUBLICATIONS

Metal-Templated Hydrogen Bond Donors as "Organocatalysts" for Carbon—Carbon Bond Forming Reactions: Syntheses, Structures, and Reactivities of 2-Guanidinobenzimidazole Cyclopentadienyl Ruthenium Complexes Alexander Scherer†, Tathagata Mukherjee‡, Frank Hampel† , and John A. Gladysx*†‡† Institut für Organische Ch.*
Balonova et al., Influencing the Optoelectronic Properties of a Heteroleptic Iridium complexby Second-Sphere H-Bonding Interactions.*
Lu, K.-Y.; Chou, H.-H.; Hsieh, C.-H.; Yang, Y.-H. O.; Tsai, H.-R.; Tsai, H.-Y.; Hsu, L.-C.; Chen, C.-Y.; Chen, I.C.; Cheng, C.-H. Wide-Range Color Tuning of Iridium Biscarbene Complexes from Blue to Red by Different $N_2N$ Ligands: An Alternative Route for Adjusting the Emission Colors. Adv. Mater. 2011, 23, 4933-4937.
Kando, A.; Hisamatsu, Y.; Ohwada, H.; Itoh, T.; Moromizato, S.; Kohno, M.; Aoki, S. Photochemical Properties of Red-Emitting Tris(cyclometalated) Iridium(III) Complexes Having Basic and Nitro Groups and Application to pH Sensing and Photoinduced Cell Death. Inorg. Chem. 2015, 54, 5342-5357.
Jiang, J.; Zhang, C.; Lin, W.; Liu, Y.; Liu, S.; Xu, Y.; Zhao, Q.; Huang, W. Long-Lived Phosphorescent Iridium (III) Complexes Conjugated with Cationic Polyfluorenes for Heparin Sensing and Cellular Imaging. Macromol. Rapid Commun. 2015, 36, 640-646.
Medina-Rodriguez, S.; Denisov, S. A.; Cudre, Y.; Male, L.; Marin-Suarez, M.; Fernandez-Gutierrez, A.; Fernandez-Sanchez, J. F.; Tron, A.; Jonusauskas, G.; McClenaghan, N. D.; Baranoff, E. High Performance Optical Oxygen Sensors Based on Iridium Complexes Exhibiting Interchromophore Energy Shuttling. Analyst 2016, 141, 3090-3097.
McDaniel, N. D.; Bernhard, S. Solar Fuels: Thermodynamics, Candidates, Tactics, and Figures of Merit. Dalt. Trans. 2010, 39, 10021-10030.
Martir, D. R.; Momblona, C.; Pertegas, A.; Cordes, D. B.; Slawin, A. M. Z.; Bolink, H. J.; Zysman-Colman, E. Chiral Iridium(III) Complexes in Light-Emitting Electrochemical Cells: Exploring the Impact of Stereochemistry on the Photophysical Properties and Device Performances. ACS Appl. Mater. Interfaces 2016, 8, 33907-33915.
Henwood, A. F.; Bansal, A. K.; Cordes, D. B.; Slawin, A. M. Z.; Samuel, I. D. W.; Zysman-Colman, E. Solubilized Bright Blue-Emitting Iridium Complexes for Solution Processed OLEDs. J. Mater. Chem. C 2016, 4, 3726-3737.
Duan, J. P.; Sun, P. P.; Cheng, C. H. New Iridium Complexes as Highly Efficient Orange-Red Emitters in Organic Light-Emitting Diodes. Adv. Mater. 2003, 15, 224-228.
Skorka, Ł.; Filapek, M.; Zur, L.; Malecki, J. G.; Pisarski, W.; Olejnik, M.; Danikiewicz, W.; Krompiec, S. Highly Phosphorescent Cyclometalated Iridium(III) Complexes for Optoelectronic Applications: Fine Tuning of the Emission Wavelength through Ancillary Ligands. J. Phys. Chem. C 2016, 120, 7284-7294.
Henwood, A. F.; Zysman-Colman, E. Lessons Learned in Tuning the Optoelectronic Properties of Phosphorescent Iridium (III) Complexes. Chem. Commun. 2017, 53, 807-826.
Chau, N.-Y.; Ho, P.-Y.; Ho, C.-L.; Ma, D.; Wong, W.-Y. Color-Tunable Thiazole-Based Iridium (III) Complexes: Synthesis, Characterization and Their OLED Applications. J. Organomet. Chem. 2017, 829, 92-100.
Xu, W.; Arieno, M.; Low, H.; Huang, K.; Xie, X.; Cruchter, T.; Ma, Q.; Xi, J.; Huang, B.; Wiest, O.; Gong, L.; Meggars, E. Metal-Templated Design: Enantioselective Hydrogen-Bond-Driven Catalysis Requiring Only Parts-per-Million Catalyst Loading. J. Am. Chem. Soc. 2016, 138, 8774-8780.

(Continued)

*Primary Examiner* — Alexander R Pagano
*Assistant Examiner* — Ebenezer O Sackey
(74) *Attorney, Agent, or Firm* — Eugene F. Derenyi; Fogler, Rubinoff LLP

(57) ABSTRACT

A method of preparing a tuned metal complex including the use of band gap tuning to change the light absorbing or light emitting properties of a metal complex. In one aspect, band gap tuning includes changing the energy gap between the conduction band and the valence band of a metal complex with a guest molecule.

11 Claims, 2 Drawing Sheets

(56) References Cited

OTHER PUBLICATIONS

Skubi, K. L.; Kidd, J. B.; Jung, H.; Guzei, I. A.; Baik, M.-H.; Yoon, T. P. Enantioselective Excited-State Photoreactions Controlled by a Chiral Hydrogen-Bonding Iridium Sensitizer. J. Am. Chem. Soc. 2017, 139, 17186-17192.

Crosby, G. A.; Demas, J. N. The Measurement of Photoluminescence Quantum Yields. J.Phys. Chem. 1971, 75, 991-1024.

Melhuish, W. H., Quantum Efficiencies of Fluorescence of Organic Substances: Effect of Solvent and Concentration of the Fluorescent Solute. J. Phys. Chem. 1961, 65, 229-235.

Greenham, N. C.; Samuel, I. D. W.; Hayes, G. R.; Phillips, R. T.; Kessener, Y. A. R. R.;Moratti, S. C.; Holmes, A. B.; Friend, R. H., Measurement of absolute photoluminescence quantum efficiencies in conjugated polymers. Chem. Phys. Lett., 1995, 241, 89-96.

Connelly, N. G.; Geiger, W. E. Chemical Redox Agents for Organometallic Chemistry.Chem. Rev. 1996, 96, 877-910.

Sheldrick, G. M. Shelxt: Integrated Space-Group and Crystal-Structure Determination. Acta Crystallogr. Sect. A 2015, 71, 3-8.

Sheldrick, G. M. Crystal Structure Refinement with SHELXL. Acta Crystallogr. Sect. C, Struct. Chem. 2015, 71 (Pt 1), 3-8.

Dolomanov, O. V; Bourhis, L. J.; Gildea, R. J.; Howard, J. A. K.; Puschmann, H. OLEX2: A Complete Structure Solution, Refinement and Analysis Program. J. Appl. Crystallogr. 2009, 42, 339-341.

Thordarson, P. Determining Association Constants from Titration Experiments in Supramolecular Chemistry. Chem. Soc. Rev. 2011, 40, 1305-1323.

Castro, A.; Martinez, A. Intramolecular Oxidative Cyclizations in Heteroarylthioureas: A Versatile Pathway to Bridgehead Heterocyclic Systems J. Heterocycl. Chem. 1999, 36, 991-995.

Vig, R.; Mao, C.; Venkatachalam, T. K.; Tuel-Ahlgren, L.; Sudbeck, E. A.; Uckun, F. M. Rational Design and Synthesis of Phenethyl-5-Bromopyridyl Thiourea Derivatives as Potent Non-Nucleoside Inhibitors of HIV Reverse Transcriptase. Bioorg. Med. Chem. 1998, 6, 1789-1797.

Ashworth, R. D. B.; Crowther, A. F. Synthetic Antimalarials; Some 2-Phenylureido- and 2-Phenylthioureido-4-Dialkylaminoalkylamino-6-Methylpyrimidines. J. Chem. Soc. 1948, 2, 581-586.

Nonoyama, M. Benzo[h]quinolin-10-yl-N Iridium (III) Complexes Bull.Chem.Soc. Jpn. 1974, 47, 767-768.

Pelphrey, P. M.; Popov, V. M.; Joska, T. M.; Beierlein, J. M.; Bolstad, E. S. D.; Fillingham, Y. A.; Wright, D. L.; Anderson, A. C. Highly Efficient Ligands for Dihydrofolate Reductase from Cryptosporidium Hominis and Toxoplasma Gondii Inspired by Structural Analysis. J. Med. Chem. 2007, 50, 940-950.

Blight, B. A.; Camara-Campos, A.; Djurdjevic, S.; Kaller, M.; Leigh, D. A.; McMillan, F. M.; McNab, H.; Slawin, A. M. Z. AAA-DDD Triple Hydrogen Bond Complexes. J. Am. Chem. Soc. 2009, 131, 14116-14122.

Rowland, R. S.; Taylor, R. Intermolecular Nonbonded Contact Distances in Organic Crystal Structures: Comparison with Distances Expected from van Der Waals Radii. J. Phys. Chem. 1996, 100, 7384-7391.

Hsu, C.-W.; Longhi, E.; Sinn, S.; Hawes, C. S.; Young, D. C.; Kruger, P. E.; De Cola, L. Pyrazolo[4,3-h] quinoline Ligand-Based Iridium(III) Complexes for Electrochemiluminescence. Chem. Asian J. 2017, 12, 1649-1658.

Rota Martir, D.; Momblona, C.; Pertegas, A.; Cordes, D. B.; Slawin, A. M. Z.; Bolink, H. J.; Zysman-Colman, E. Chiral Iridium(III) Complexes in Light-Emitting Electrochemical Cells: Exploring the Impact of Stereochemistry on the Photophysical Properties and Device Performances. ACS Appl. Mater. Interfaces 2016, 8, 33907-33915.

Kim, J. II; Shin, I.-S.; Kim, H.; Lee, J.-K. Efficient Electrogenerated Chemiluminescence from Cyclometalated Iridium (III) Complexes. J. Am. Chem. Soc. 2005, 127, 1614-1615.

Alexander Scherer, Tathagata Mukherjee, Frank Hampel, and John A. Gladysz. Metal-Templated Hydrogen Bond Donors as "Organocatalysts" for Carbon-Carbon Bond Forming Reactions: Syntheses, Structures, and Reactivities of 2-Guanidinobenzimidazole Cyclopentadienyl Ruthenium Complexes. Organometallics 2014, 33, 6709-6722.

Shin-Ya Takizawa et al. "Phosphorescent Iridium Complexes Based on 2-Phenylimidazo[1,2-a]pyridine Ligands: Tuning of Emission Color toward the Blue Region and Application to Polymer Light-Emitting Devices" Inorg. Chem., 2007, 46 (10), pp. 4308-4319.

Stefano Stagni et al "Essential Role of the Ancillary Ligand in the Color Tuning of Iridium Tetrazolate Complexes", Inorg. Chem., 2008, 47 (22), pp. 10509-10521.

* cited by examiner

METAL COMPLEXES AND METHODS OF PREPARING THE SAME

FIELD

The present invention relates to metal complexes and methods of preparing the same.

BACKGROUND

Metal complexes and, in particular, the tuning of metal complexes are of interest. Tuning can be used to change the light absorbing or light emitting properties of a metal complex. With respect to light emission, Cyclometalated $Ir^{III}$ complexes are under intense investigation due to their high photoluminescence (PL) efficiency, relatively short PL lifetimes and wide range of accessible colors across the visible spectrum.[1] These complexes have been used in myriad applications such as biological labelling agents,[2] oxygen sensors,[3] photocatalysts for hydrogen production,[4] and as emitters in electroluminescent devices.[5] Notably, color tuning of these complexes is typically achieved through the modification or functional group substitution of ancillary and/or cyclometalating ligands.[6] Until recently, hydrogen bonding in iridium complexes have been limited to H-bonds aimed at structure retention for biomimetic organo- and photocatalysis.[7]

BRIEF DESCRIPTION OF THE DRAWINGS

The invention is described below in greater detail with reference to the accompanying drawings which illustrate preferred embodiments of the invention, and wherein.

DESCRIPTION

Figure 1:
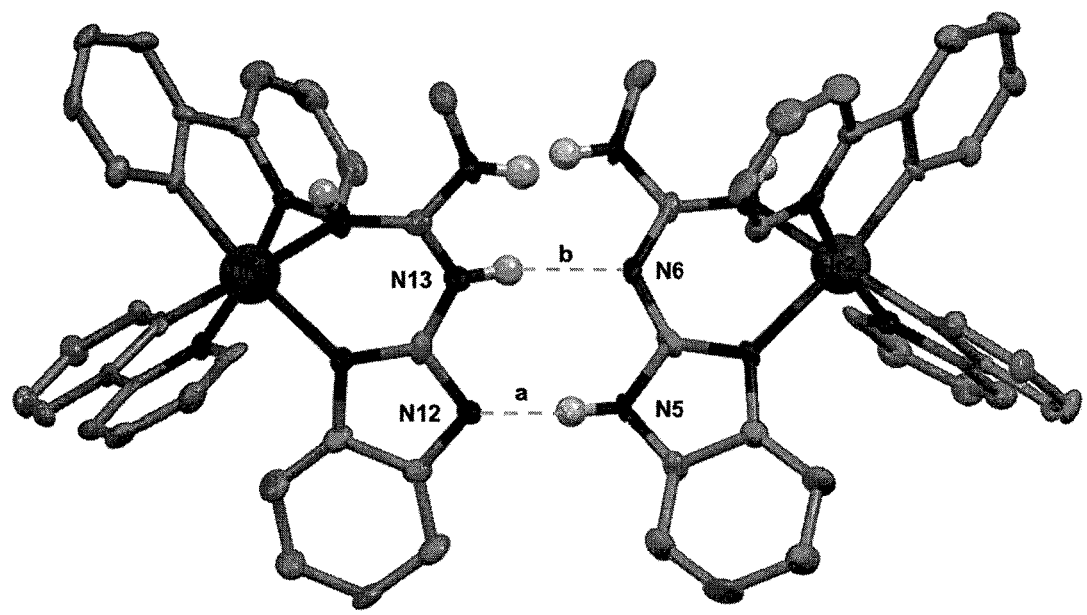
FIG. 1 depicts the X-ray crystal structure of complex 1.

In one embodiment, the present invention relates to a method of preparing a tuned metal complex including the use of band gap tuning to change the light absorbing or light emitting properties of a metal complex. In one aspect, band gap tuning includes changing the energy gap between the conduction band and the valence band of a metal complex with a guest molecule.

In another embodiment, the present invention relates to a metal complex represented by the following general structures:

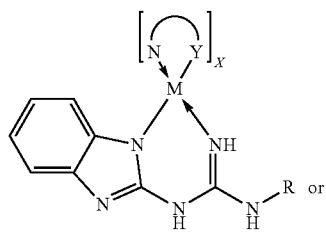

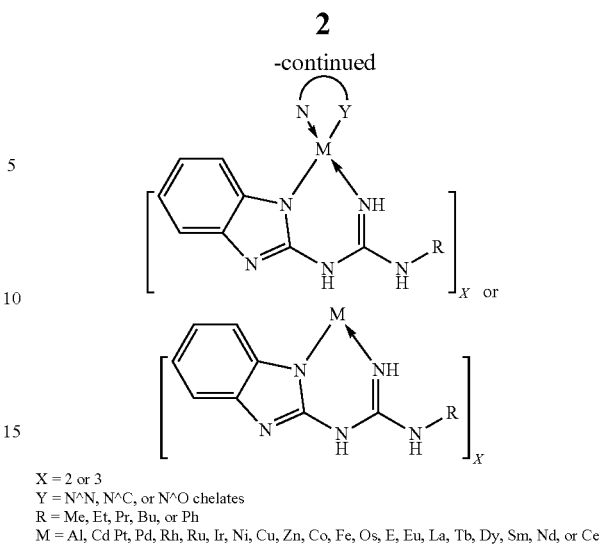

X = 2 or 3
Y = N^N, N^C, or N^O chelates
R = Me, Et, Pr, Bu, or Ph
M = Al, Cd Pt, Pd, Rh, Ru, Ir, Ni, Cu, Zn, Co, Fe, Os, E, Eu, La, Tb, Dy, Sm, Nd, or Ce In one aspect, the metal complex is a transition metal. In one aspect, the transition metal is an iridium (III) complex. In other aspects, the iridium (III) complex has one of the following structures:

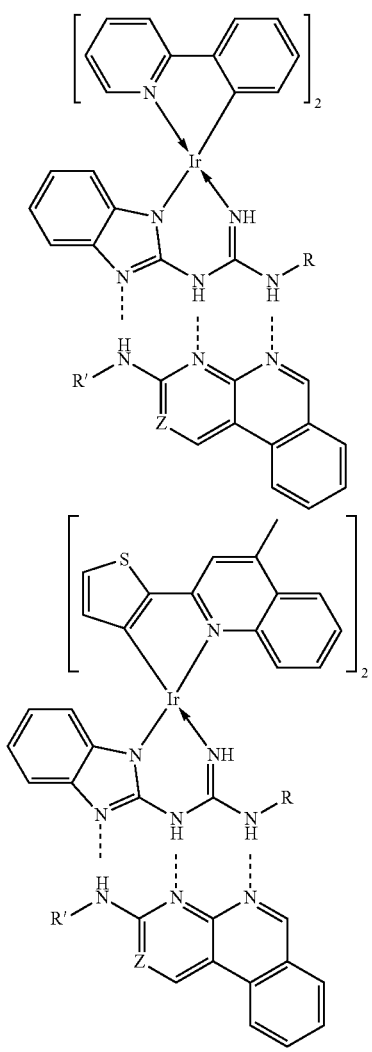

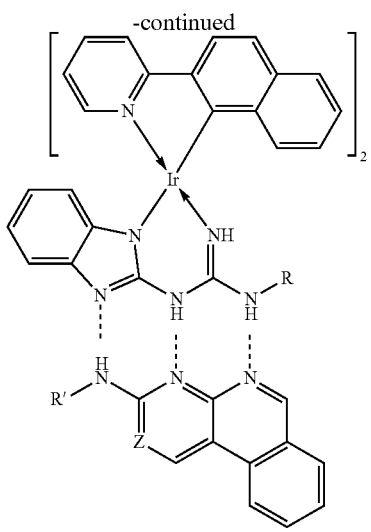

R = Me, Et, Pr, Bu, or Ph
R' = H, Me, Et, Pr, Bu, or Ph
Z = N or C

In another embodiment, the present invention relates to a ligand having the following structure:

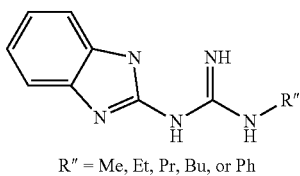

R″ = Me, Et, Pr, Bu, or Ph

In another embodiment, the present invention relates to use of the ligand for altering the energy gap between a conductive band and a valence band in a metal complex having the following structure:

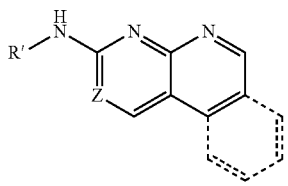

R' = H, Me, Et, Pr, Bu, or Ph
Z = N or C

In another embodiment, the present invention relates to a method of preparing a color tuned iridium complex including the use of a second-sphere coordination. Color tuning refers to influencing emission properties of phosphorescent iridium complexes. In another aspect, the use of a complimentary H-bonding guest molecule binding through contiguous triple H-bonding interactions can induce a shift in the emission of an iridium complex from green to blue, yellow to blue, or red to blue without the need to alter the ligand structure around the metal centre, while simultaneously increasing the photoluminescence quantum yield in solution. The association constant for this host-guest interaction is determined to be $K_a = 4.3 \times 10^3$ $M^{-1}$ in a solution of 2% dimethylsulfoxide in chloroform.

In another embodiment, the present invention relates to a method of producing an iridium complex where chromophoric units are assembled into higher-order structures via H-bonding, formed from a neutral N^N guanidine-chelated iridium (III) complex. Methods according to embodiments of the present invention can be used to produce multinuclear assemblies incorporating tunable PL properties.

In another embodiment, the present invention relates to a method for tuning the emission properties of iridium (III) complexes ($Ir^{III}$ complexes) using direct second-sphere coordination.

In another embodiment, the present invention relates to an iridium (III) complex having the following structure:

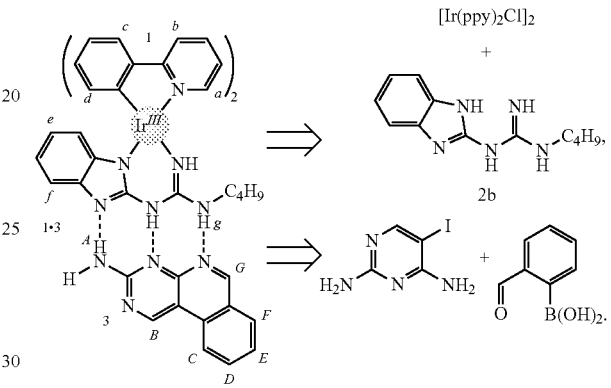

where complex 1 is host, complex 2 is ligand, complex 3 is guest, and complex 1•3 is a host-guest complex. A limited retrosynthetic analysis of the components complex 1, complex 2 and complex 3 is provided to the right of complex 1•3. The triple H-bonded heterodimeric system in complex 1•3 exhibits modulated photophysical properties from that of the corresponding mononuclear cyclometalated $Ir^{III}$ (complex 1).

Synthetic Procedures

According to an embodiment, the present invention relates to a method of preparing a ligand 2b through a steps of a synthetic sequence, including the reaction formula of Scheme 1. In another embodiment, the present invention relates to a method of preparing an iridium complex 1 through a synthesis of steps, including the reaction formula of Scheme 2:

Scheme 1

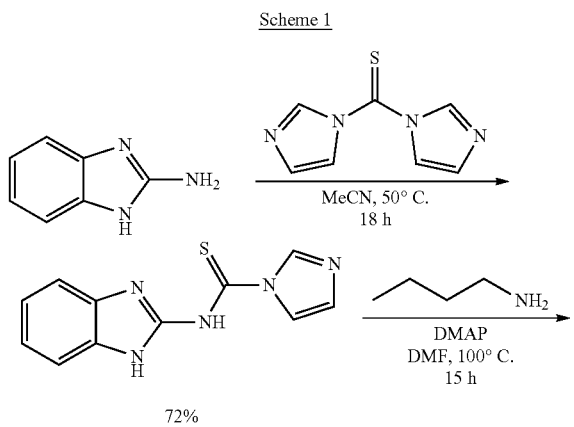

72%

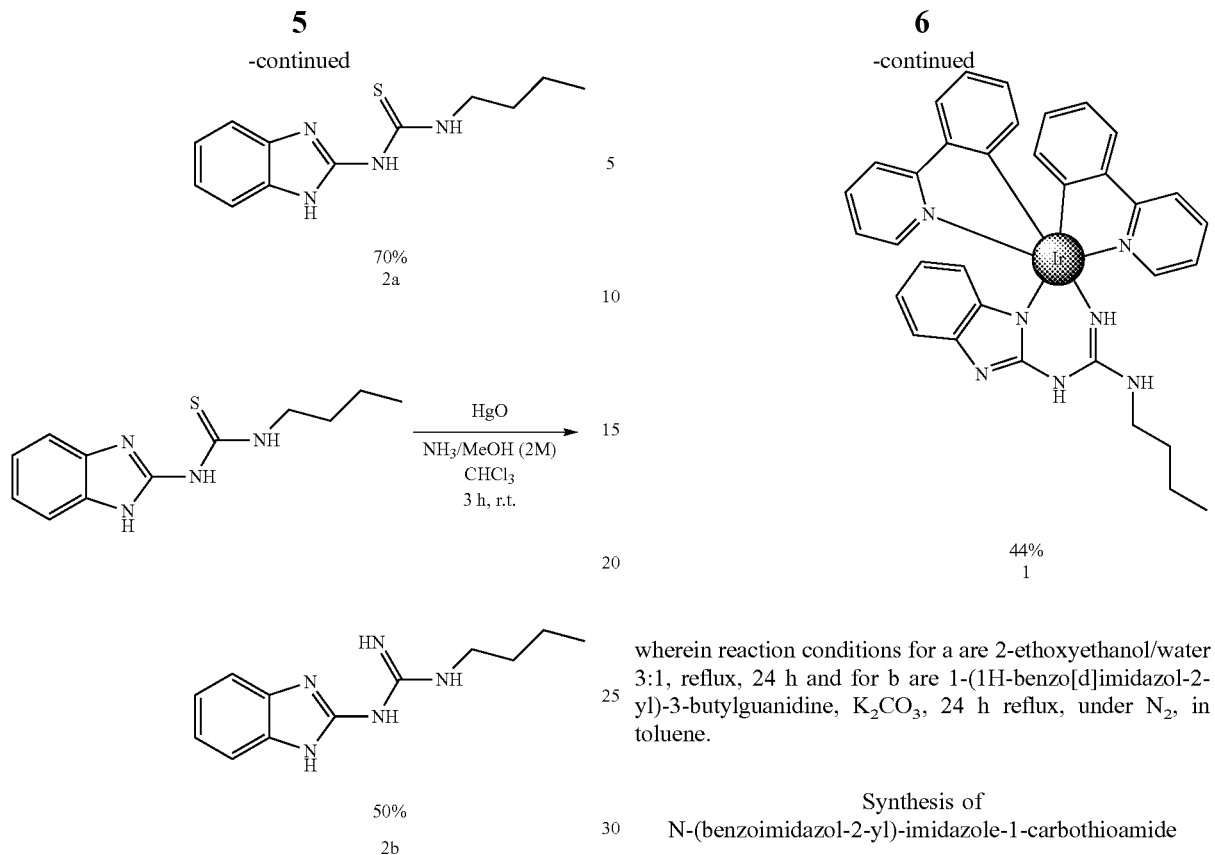
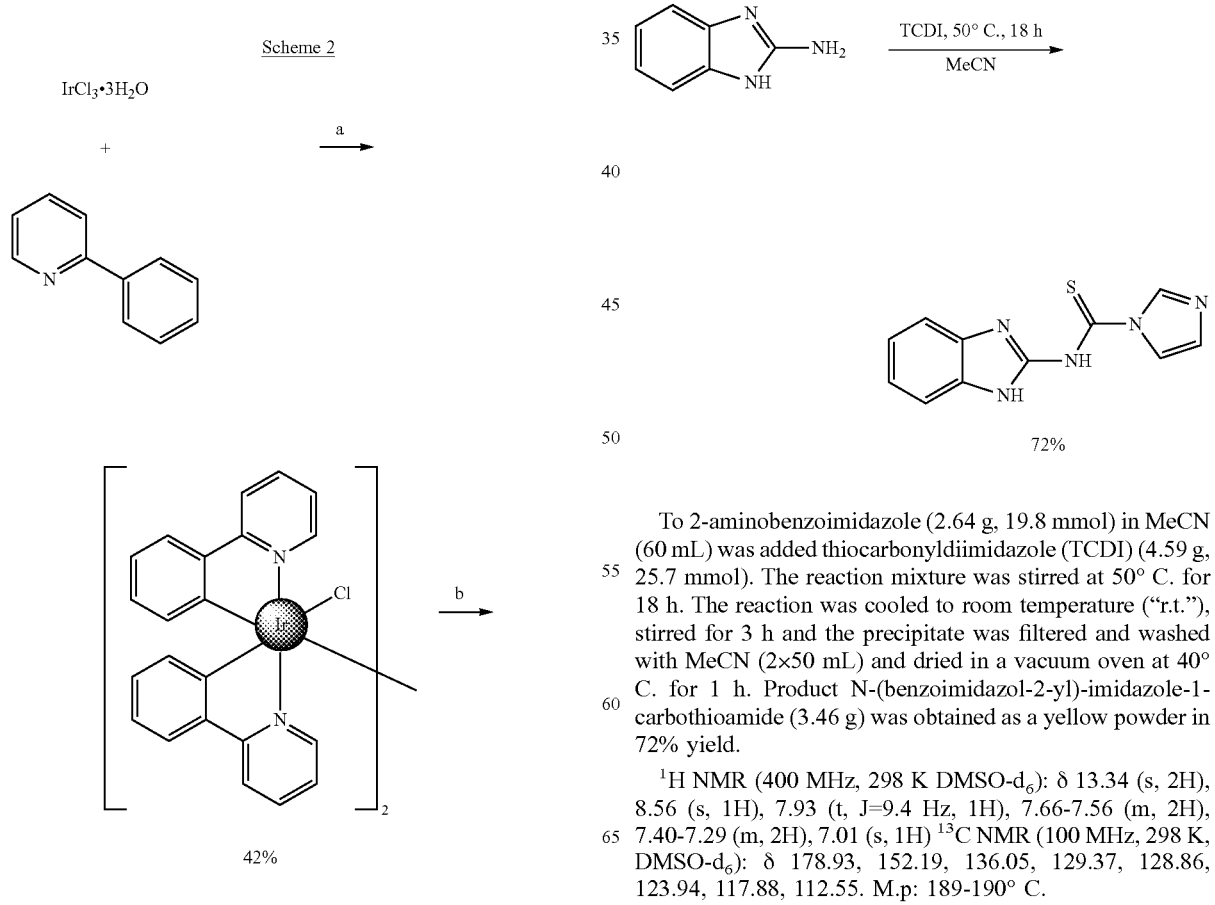

wherein reaction conditions for a are 2-ethoxyethanol/water 3:1, reflux, 24 h and for b are 1-(1H-benzo[d]imidazol-2-yl)-3-butylguanidine, $K_2CO_3$, 24 h reflux, under $N_2$, in toluene.

Synthesis of N-(benzoimidazol-2-yl)-imidazole-1-carbothioamide

To 2-aminobenzoimidazole (2.64 g, 19.8 mmol) in MeCN (60 mL) was added thiocarbonyldiimidazole (TCDI) (4.59 g, 25.7 mmol). The reaction mixture was stirred at 50° C. for 18 h. The reaction was cooled to room temperature ("r.t."), stirred for 3 h and the precipitate was filtered and washed with MeCN (2×50 mL) and dried in a vacuum oven at 40° C. for 1 h. Product N-(benzoimidazol-2-yl)-imidazole-1-carbothioamide (3.46 g) was obtained as a yellow powder in 72% yield.

$^1$H NMR (400 MHz, 298 K DMSO-$d_6$): δ 13.34 (s, 2H), 8.56 (s, 1H), 7.93 (t, J=9.4 Hz, 1H), 7.66-7.56 (m, 2H), 7.40-7.29 (m, 2H), 7.01 (s, 1H) $^{13}$C NMR (100 MHz, 298 K, DMSO-$d_6$): δ 178.93, 152.19, 136.05, 129.37, 128.86, 123.94, 117.88, 112.55. M.p: 189-190° C.

Synthesis of Compound Dichlorotetrakis[2-2-pyridyl)phenyl]diiridium(III)

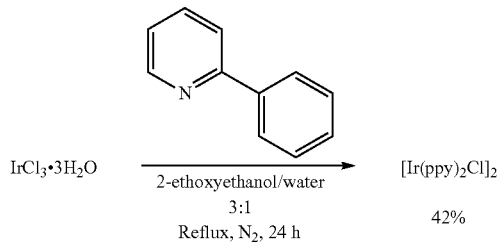 [SMILES: c1ccc(-c2ccccn2)cc1]

The ligand 2-phenylpyridine (0.69 mL, 4.85 mmol) and iridium (III) chloride trihydrate (0.81 g, 2.31 mmol) were dissolved in 2-ethoxyethanol (15 mL) and water (5 mL). The reaction mixture was refluxed for 24 h under a nitrogen atmosphere. After cooling to room temperature, the yellow precipitate was filtered via Buchner and thoroughly washed with water (20 mL), ethanol (20 mL) and acetone (20 mL), dried on air and later in vacuum oven (40° C., 24 h). Final product (1.05 g) was obtained as a canary yellow colored powder with 42% yield and used in further steps without further purification. $^1$H NMR (400 MHz, 298 K, chloroform-d): δ 9.24 (d, J=5.8 Hz, 2H), 7.87 (d, J=8.1 Hz, 2H), 7.78-7.68 (m, 2H), 7.50 (t, J=8.6 Hz, 2H), 6.81-6.69 (m, 4H), 6.61-6.51 (m, 2H), 5.93 (d, J=7.8 Hz, 2H). $^{13}$C NMR (100 MHz, 298 K, chloroform-d): δ 168.97, 152.13, 145.79, 144.14, 136.61, 131.03, 129.54, 124.05, 122.57, 121.28, 118.85.

Experimental Section

Materials

All starting materials were purchased from commercial sources and used without further purification. Analytical thin layer chromatography was done on precoated TLC sheets Alugram Sil G/UV254. Column chromatographic purifications were done with silica gel, ultra-pure, 60-200 micrometer (60 Å) or aluminum oxide (activated, neutral) as specified. All experiments were performed under a dry $N_2$ atmosphere using standard Schlenk techniques unless otherwise noted. All materials were used in the condition as received from the supplier without further purification unless otherwise noted.

NMR $^1$H (400 MHz) and $^{13}$C (100 MHz) NMR spectra were recorded on a 'JEOL ECS 400' spectrometer in deuterated solvents such as chloroform-d, DMSO-$d_6$ or methanol-$d_4$ as noted. All chemical shifts are reported in δ (ppm) referenced to tetramethylsilane, Si(CH$_3$)$_4$, while peak multiplicities are referred to as singlet (s), doublet (d), triplet (t), quartet (q), broad singlet (bs), and multiplet (m).

Mass Spectrometry, Infrared, Elemental and Melting Point Analyses

High-resolution mass spectral data were recorded on a Bruker MicrOTOF-Q II Instrument. IR spectra were recorded using a Shimadzu IRAffinity-1 spectrophotometer. Elemental analysis was performed by the Elemental Analysis Service at the London Metropolitan University, UK. Melting points were determined on a Buchi Melting Point Instrument.

UV-Visible Absorption

Absorption spectra were recorded at room temperature using a Shimadzu UV-1800 double beam spectrophotometer. Molar absorptivity determination was verified by linear least-squares fit of values obtained from at least four independent solutions at varying concentrations ranging from $2.8 \times 10^{-4}$ to $2.4 \times 10^{-5}$ M.

Photoluminescence Analyses

Steady-state emission and excitation spectra and time-resolved emission spectra were recorded at 298 K using an Edinburgh Instruments F980. All samples for steady-state measurements were excited at 360 nm and the samples for time-resolved measurements at 378 nm using a PDL 800-D pulsed diode laser. Photoluminescence quantum yields (PLQY) were determined using the optically dilute method, [8] using quinine sulfate as a reference (54.6%; 0.5 M $H_2SO_4$).[9] The PLQY of each component and the co-complex are the average values measured in triplicate and the estimated error is 5%. Photoluminescence quantum yield measurements of thin films were performed in an integrating sphere under a nitrogen purge in a Hamamatsu C9920-02 luminescence measurement system.[10] The details of all PL analyses are provided in the next section.

Electrochemistry

Cyclic voltammetry (CV) measurements were performed in an Innovative Technology glovebox using a standard three electrode system connected to a Biologic SP-150 potentiostat. Solutions for CV were prepared in DCM solution with 0.1M of tetrabutylammonium hexfluorophosphate (TBAPF$_6$) as the electrolyte at 298 K. The cells consisted of a platinum disk working electrode (0.07 cm$^2$), a platinum wire counter electrode, and an Ag/Ag$^+$ reference electrode. Concentration of active species: 2 mM, potential range 0-2.2 V, scan rate 100 mV s$^{-1}$. Recrystallized ferrocene was used as the internal standard and all potentials are reported vs SCE [11] using the formal potential of ferrocene/ferrocenium in DCM, which is 0.46 V vs SCE [11] in 0.1 m TBAPF$_6$ solution.

Single Crystal X-Ray Diffraction $C_{35}H_{33}Cl_3IrN_7$ (M=850.23 g/mol): triclinic, space group P-1 (no. 2), a=14.4927(8) Å, b=15.4171(11) Å, c=17.5785 (11) Å, α=103.021(6)°, β=103.260(5)°, γ=112.155(6)°, V=3322.1(4) Å$^3$, Z=4, T=100.00(10) K, μ(MoKα)=4.298 mm$^{-1}$, Dcalcc=1.700 g/cm$^3$, 58513 reflections measured (4.584°≤2Θ≤59.302°), 16652 unique (R$_{int}$=0.0993, R$_{sigma}$=0.1330) which were used in all calculations. The final R$_1$ was 0.0623 (I>2σ(I)) and wR$_2$ was 0.1110 (all data). Suitable crystals were grown by slow vapour diffusion of hexanes into a solution of 1 dissolved in CHCl$_3$ and mounted on a Rigaku Oxford Diffraction Supernova diffractometer. The data was refined by least squares minimization using ShelXL[12] and solved by intrinsic phasing using ShelXT. [13] Olex2 [14] was used as an interface to all ShelX programs. Hydrogen atoms located on N6, N13, N5 and N12 could not be located from the difference map. To ensure a chemically sensible model, hydrogen atoms were modelled at calculated positions for all four possible locations, and occupancy was fixed at 50% in all cases. The butyl chain on one of the two independent molecules is disordered, along with one molecule of chloroform over two positions, each with 50% occupancy. CCDC 1822594 contains the supplemental crystallographic information and is available free of charge from the Cambridge Crystallographic Database.

Host-Guest Titrations

All dilutions and titrations were performed using Hamilton Gastight microliter syringes at room temperature. NMR dilution studies of complex 1 (5×10$^{-3}$ M) were performed in CD$_2$Cl$_2$ with addition of appropriate aliquots of CD$_2$Cl$_2$. UV-Vis dilution studies of complex 1 (6×10$^{-5}$ M) were performed in HPLC grade dichloromethane with addition of appropriate aliquots of HPLC grade dichloromethane. UV- Vis titration studies were performed with host 1 ($1\times10^{-5}$ M) and titrated with the addition of appropriate aliquots of a solution of guest 3 ($1\times10^{-4}$ M) with a background concentration of host ($1\times10^{-5}$ M) to maintain a constant concentration of host throughout the study. All dilution and titration data were analyzed with the program BindFit [15,16].

Synthesis. 1-(1H-benzo[d]imidazole-2-yl)-3-butylthiourea 2a

Compound 2a is known [17] but was synthesized using an alternative modified procedure.[18] To a solution of N-(benzoimidazol-2-yl)-imidazole-1-carbothioamide (0.46 g, 1.9 mmol) in DMF (20 mL) was added 0.1 equiv. of 4-N,N-dimethylaminopyridine followed by dropwise addition of n-butyl amine (0.19 mL, 1.9 mmol) while stirring. The reaction mixture was stirred at 100° C. for 15 h. After cooling down to r.t. the reaction mixture was poured into ice-cold water and stirred for 1 h. A white-milky color precipitate was filtered and was washed with water (2×15 mL) and further purified by column chromatography (EtOAc/hexane, 3:2. $R_f$=0.2). Fractions were collected and the solvent removed by rotary evaporation. The product 2a was dried in a vacuum oven at 40° C. overnight. Pale yellow title compound was obtained in 70% yield. $^1$H NMR (400 MHz, 298 K, DMSO-$d_6$): δ 11.13 (t, 3H, J=58.7 Hz), 7.44 (s, 2H), 7.19-7.04 (m, 2H), 3.64 (d, 2H, J=5.8 Hz), 1.69-1.53 (m, 2H), 1.46-1.32 (m, 2H), 0.92 (dt, 3H, J=19.3, 6.7 Hz). $^{13}$C NMR (100 MHz, 298 K, DMSO-$d_6$): δ 177.82, 148.19, 140.39, 131.32, 121.78, 116.91, 111.45, 44.36, 39.52, 30.59, 19.94, 13.92. M.p. 147-150° C. EI-MS m/z calculated: 247.10 found: 248.11 [M+]. Anal. calcd. for $C_{12}H_{16}N_4S$: C, 58.04; H, 6.49; N, 22.56. Found: C, 57.93; H, 6.54; N, 22.40.

1-(1H-benzo[d]imidazole-2-yl)-3-butylguanidine 2b

From a modified procedure,[19] compound 2a (269 mg, 1.08 mmol) was suspended in 15 mL of $CHCl_3$ and to this were added HgO (0.32 g, 1.51 mmol) and 2 M methanolic $NH_3$ (6 mL). The reaction mixture was stirred at r.t. for 3 h and a color change from wine red to brown was observed. The reaction was then filtered through celite and concentrated under reduced pressure. The resulting solid was dissolved in 2 M acetic acid (~8 mL) and stirred for 1 h, then filtered through celite. The pH was adjusted to 8.0 by addition of a 10 M solution of NaOH. The formed precipitate was filtered, washed with water and dried. The product was dissolved in chloroform and extracted 3× with saturated solution of $NaHCO_3$. The organic phase was separated and dried over $MgSO_4$ and the solvent removed under reduced pressure. The final product was dried overnight in a vacuum oven at 40° C. Title compound 2b was obtained as white powder in 50% yield. $^1$H NMR (400 MHz, 298 K, DMSO-$d_6$): δ 11.00 (s, 1H), 7.20 (d, 1H, J=7.3 Hz), 7.07 (d, 1H, J=7.1 Hz), 6.98-6.78 (m, 2H), 3.21 (dd, 2H, J=12.7, 6.9 Hz), 1.48 (dd, 2H, J=14.8, 7.3 Hz), 1.36 (dt, 2H, J=14.7, 7.2 Hz), 0.92 (t, 3H, J=7.3 Hz). $^{13}$C NMR (100 MHz, 298K, DMSO-$d_6$): δ 159.05, 157.66, 142.59, 132.21, 119.65, 118.99, 114.94, 108.48, 40.07, 39.52, 31.49, 19.66, 13.80. M.p. 190-208° C. EI-MS m/z calculated: 231.15 found: 232.16 [M+]. Anal. calcd. for $C_{12}H_{17}N_5$: C, 62.31; H, 7.41; N, 30.28. Found: C, 62.12; H, 7.55; N, 30.06.

Iridium Complex 1

The iridium dimer complex [Ir(ppy)$_2$Cl]$_2$ (39.7 mg, $3.70\times10^{-5}$ mol),[20] guanidine 2b (13.2 mg, 2.5 equiv.) and potassium carbonate (50 mg, 10 equiv.) were added to 12 mL of dry toluene. The reaction mixture was stirred overnight at 110° C. under a $N_2$ atmosphere. The solvent was removed under reduced pressure. A small amount of dichloromethane was added to dissolve the solid (8-12 mL) and the mixture was extracted with water (3×20 mL) to remove the excess base. The organic layers were combined and the solvent removed under reduced pressure. Further purification included precipitation and column chromatography (silica gel, DCM/MeOH, 10:0.25-10:1, $R_f$=0.3). Final product 1 was obtained as a bright yellow powder in 88% yield. $^1$H NMR (600 MHz, 298 K, chloroform-d): δ 8.68 (dd, 1H, J=5.9, 0.8 Hz), 8.15-8.04 (m, 1H), 7.88 (d, 1H, J=8.1 Hz), 7.78 (d, 1H, J=8.0 Hz), 7.73 (td, 1H, J=8.0, 1.6 Hz), 7.67 (dd, 1H, J=7.4, 1.3 Hz), 7.60 (d, 2H, J=7.8 Hz), 7.15 (d, 1H, J=7.9 Hz), 7.08 (ddd, 1H, J=7.3, 5.9, 1.3 Hz), 7.01-6.87 (m, 4H), 6.79 (dtd, 2H, J=20.6, 7.4, 1.3 Hz), 6.68-6.62 (m, 1H), 6.43 (dd, 1H, J=7.6, 0.8 Hz), 6.24-6.19 (m, 1H), 6.15 (s, 1H), 6.09 (d, 1H, J=8.3 Hz), 5.72 (s, 1H), 4.56 (s, 1H), 3.04-2.78 (m, 2H), 1.41 (ddd, 2H, J=14.0, 7.1, 3.5 Hz), 1.23 (dd, 2H, J=14.0, 6.6 Hz), 0.79 (t, 3H, J=7.3 Hz). $^{13}$C NMR (100 MHz, 298K, chloroform-d): δ 169.15, 168.17, 153.61, 151.88, 151.57, 150.01, 148.83, 147.52, 144.62, 144.47, 141.20, 136.82, 136.51, 133.05, 132.01, 129.72, 124.57, 124.01, 122.63, 121.84, 121.62, 121.33, 121.08, 118.80, 116.86, 110.65, 77.16, 41.06, 30.85, 20.05, 13.76. EI-MS m/z calculated: 731.2348 found: 732.2450 [M+]. Anal. calcd. for $C_{34}H_{32}IrN_7$: C, 55.87; H, 4.41; N, 13.41. Found: C, 55.96; H, 4.31; N, 13.35.

Pyrimido-[4,5-c]isoquinolin-3-amine 3

5-iodopyrimidine-2,4-diamine (197 mg, $8.34\times10^{-4}$ mol), 2-formylphenyl boronic acid (182 mg, 1.21 mmol), potassium carbonate (0.461 g, 3.33 mmol) and tetrakis(triphenylphosphine)palladium(0) (1.4 mg, 0.5 mol %) were added to the mixture of dioxane and water (3:1, 9 mL of dioxane, 3 mL of water). The reaction mixture was heated under reflux for 3 h, then cooled to r.t. and placed in cold bath. The precipitate filtered and washed with water (2×30 mL), three times suspended and sonicated in water and filtered, then finally dried in a vacuum oven (24 h, 40° C.). Product 3 (82 mg) was obtained as a fine bright yellow powder in 50% yield. $^1$H NMR (400 MHz, 298K, DMSO-$d_6$): δ 9.88 (s, 1H), 9.50 (s, 1H), 8.72 (d, 1H, J=8.1 Hz), 8.17 (d, 1H, J=7.5 Hz), 7.92 (ddd, 1H, J=8.4, 7.3, 1.3 Hz), 7.70-7.63 (m, 1H), 7.18 (s, 2H). $^{13}$C NMR (100 MHz, 298 K, DMSO-$d_6$): δ 163.68, 161.43, 158.80, 158.50, 132.58, 132.22, 129.33, 126.43, 124.43, 124.41, 120.35, 107.00. EI-MS m/z calculated: 196.07 found: 197.08 [M+]. M.p.>280° C. Anal. calcd. for $C_{11}H_8N_4$: C, 67.34; H, 4.11; N, 28.55. Found: C, 67.19; H, 4.25; N, 28.35.

Results and Discussion

Complex 1 was synthesized by refluxing benzimidazolylguanidine 2b with the iridium μ-chloro-bridged dimer [Ir(ppy)$_2$Cl]$_2$ (ppyH=2-phenylpyrdine) [20] in the presence of an excess of base in toluene. Isolation, after purification by column chromatography, yielded 1 as a yellow solid. Compound 3 was prepared by reacting 2, 4-diamino-5-iodopyrimidine [21] with 2-formylphenylboronic acid, following a modified tandem Suzuki-Miyaura cross-coupling/imine condensation/cyclization procedure.[22]

Single crystals of 1 suitable for X-ray diffraction study were obtained by slow vapour diffusion of hexanes into a chloroform solution of 1. Referring to FIG. 1, complex 1 crystallized in the triclinic space group P-1 as a H-bonded dimer with annotated NH . . . N contacts (orange); a) N5 . . . N12=2.76 Å, NH . . . N=158°; b) N6 . . . N12=2.91 Å, NH . . . N=161°. All CH-hydrogens and butyl chain are omitted for clarity. Thermal ellipsoids are set to 50% probability. As expected, the central iridium atoms of the dimer are bonded to two ppy ligands via bidentate C^N ligation with the nitrogen atoms in a mutually trans configuration, and to the guanidine benzimidazolate ligand 2b as a 6-membered N^N⁻ chelate. Of interest to us are the observed intermolecular N5 . . . N12 and N6 . . . N13 contact distances (a=2.76 Å, b=2.91 Å), which are less than the sum of van der Waals radii (characteristic for this type of interaction), and an affirmation of a previous approach. [23] Given this result in the solid-state, we proceeded to quantify this interaction in solution using both UV-Vis absorption and $^1$H NMR dilution experiments.

Figure 2:
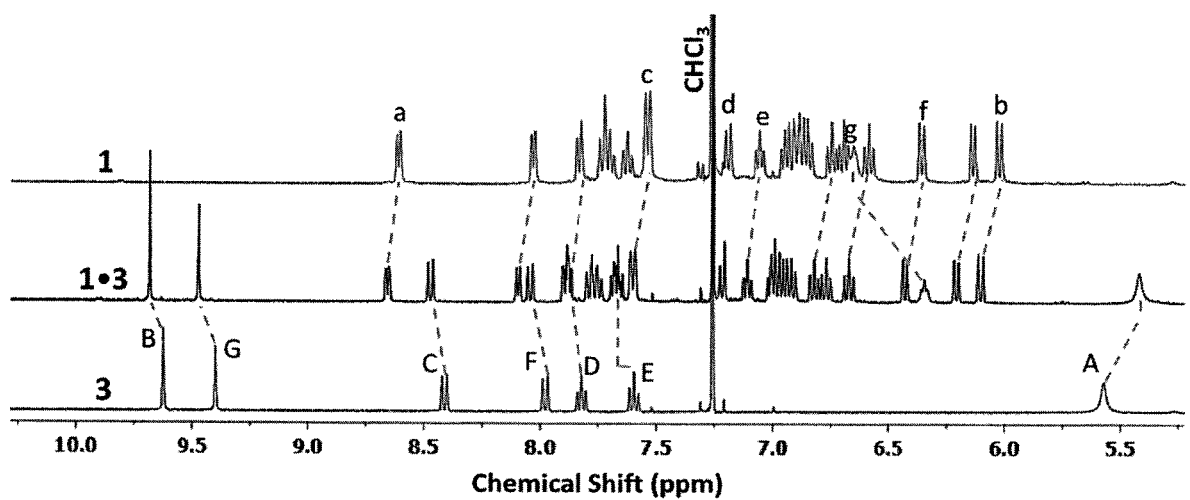
FIG. 2 is a comparison of $^1H$ NMR stacked spectra.

The overall dimerization constant was determined by UV-Vis absorption studies to be $K_d$=25 M$^{-1}$ in dichloromethane, which was confirmed by $^1$H NMR in $CD_2Cl_2$ ($K_d$=23 M$^{-1}$).[15] This suggests that a high concentration, on the order of 10$^{-2}$ M, is required for 1 to homodimerize in DCM, and thus a minimal destructive energy is sufficient to disassemble the dimer in DCM to form the proposed triple H-bonding heterodimeric system 1•3. It was expected that 1•3 would form a stronger interaction than the homodimer structure of 1, which is merely comprised of two alternating H-bonds. Indeed, the enthalpy gained in introducing additional interactions can influence the complexation strength in 1•3, particularly when the effects of secondary attractive and/or repulsive interactions are considered. Adduct 1•3 can be described by a H-bond donor (D) and acceptor (A) arrangement comprising of a contiguous AAD-DDA array. The strength of the association of this heterodimeric system was assessed by UV-Vis absorption titration of 1 with 3 (CHCl$_3$/DMSO 98:2), revealing an association constant of $K_a$=4.3×10$^3$ M$^{-1}$.[15]. A comparison of $^1$H NMR stacked spectra is presented in FIG. 2. On the left side of FIG. 2: $^1$H NMR (400 MHz, 1×10$^{-3}$ M, CDCl$_3$, 298 K) comparison in chloroform-d: compound 1 (green—top graph); complex 1•3; (black—middle graph); compound 3 (blue—bottom graph). On the right hand side of FIG. 2: demonstration of chromaticity shift with increasing mole percentage of 3 to a DCM solution of 1 under ambient and UV (365 nm) light. Dashed lines in FIG. 2 show shifts upon formation of complex 1•3.

Figure 3:
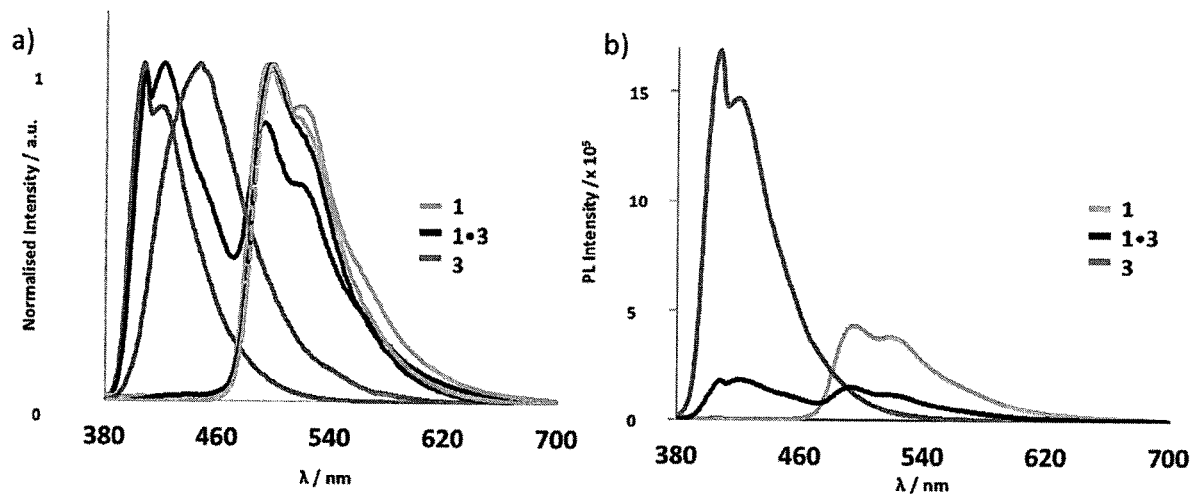
FIGS. 3(a-b) are emission spectra.

A comprehensive photophysical study of assembly 1•3 and its individual components was undertaken in DCM solution and as 5 wt % polymethylmetacrylate (PMMA) doped films (FIGS. 3a)-c). FIG. 3a) shows normalized emission spectra of solution (DCM at 5×10$^{-5}$ M; solid lines) and solid state (PMMA films; dashed lines) of 1 (green), 3 (blue) and 1•3 (black); inset: photos of PMMA films deposited on quartz slides ($\lambda_{ex}$=360 nm). FIG. 3b) shows non-normalized emission spectra in DCM (5×10$^{-5}$ M) illustrating quenching phenomenon with addition of 3 to 1; inset: photos of DCM solution in quartz cuvettes. FIG. 3c) shows absorption (solid black line) and corrected PL excitation (red dashed line; measured at 580 nm) spectra normalized to absorbance at 430 nm. The UV-vis absorption spectra of 1 and 1•3 in DCM show intense bands at 250-300 nm that are assigned to the spin-allowed π-π* transitions. The weaker bands at wavelengths longer than 320 nm result from both singlet and triplet metal-to-ligand (Ir(dπ) to C^N) and ligand-to-ligand (N^N to C^N) charge transfer ($^1$MLCT/LLCT) transitions and the complex shows comparable behavior to other neutral iridium complexes containing two ppy C^N ligands.[24] The photophysical properties of 1, 1•3 and 3 are summarized in Table 1 and their emission spectra are illustrated in FIG. 3(a) and FIG. 3(b). Complex 1 is a green emitter with a $\lambda_{PL}$ at 491 nm and a shoulder peak at 518 nm ($\Phi_{PL}$=20%), indicative of an emission from a ligand-centered state. The mono-exponential emission lifetime ($\tau_{PL}$) of 0.70 μs observed for 1 ($\lambda_{ex}$=378 nm) indicates the presence of a single emissive species. The emission of 1 in the PMMA-doped film is modestly bathochromically shifted to 498 nm and the $\Phi_{PL}$ of 1 is enhanced in the solid state to 34%.

TABLE 1

Photophysical and electrochemical data for complexes 1, 3 and 1 · 3.[a]

| Complex | $\lambda_{PL}$/nm | CIE/x,y | $\tau_{PL}$[b]/μs | $\Phi_{PL}$[c] | $k_r^d$/s$^{-1}$ | $k_{nr}^d$/s$^{-1}$ | $E_{ox}^e$/V |
|---|---|---|---|---|---|---|---|
| 1 | 491, 518 | 0.23, 0.56 | 0.70 | 0.20 | 2.8 × 10$^5$ | 1.1 × 10$^6$ | 1.12 |
|   | (498, 518) | (0.20, 0.59) | (0.4, 1.7) | (0.34) | (2.0 × 10$^5$) | (3.8 × 10$^5$) |   |
| 1 · 3 | 425, 494 | 0.18, 0.20 | 0.33, 0.75 | 0.25 | 3.3 × 10$^5$ | 1.3 × 10$^6$ | 1.17 |
|   | (497) | (0.19, 0.56) | (0.3, 1.6) | (0.23) | (1.4 × 10$^5$) | (4.8 × 10$^5$) |   |
| 3 | 409, 426 | 0.15, 0.03 | 3.0 × 10$^{-3}$ | 0.43 | 2.1 × 10$^8$ | 2.9 × 10$^8$ | 1.65 |
|   | (446) | (0.15, 0.08) | (1 × 10$^{-3}$, 4 × 10$^{-3}$) | (0.07) | (1.6 × 10$^7$) | (2.3 × 10$^8$) |   |

[a]Solution data are reported in degassed DCM. Solid state data are represented in parentheses. Polymer doped films were prepared with 5% of emitter and 95% PMMA in 2-methoxyethanol and deposited by spin-coating on quartz substrate. 1 · 3 complex is 1:1 ratio of iridium complex 1 and compound 3. All samples excited at 360 nm.
[b]Emission lifetimes were collected by excitation at $\lambda_{ex}$ = 378 nm. $\lambda_{em}$ used to collect decay lifetimes are reported in the SI, Section 5, FIG. S20-S26.
[c]Quinine sulfate employed as the external reference ($\Phi_{PL}$ = 54.6% in 0.5M H$_2$SO$_4$ at 298K).[11]
[d]$k_r$ and $k_{nr}$ were calculated using the major lifetime component.
[e]Measurements were carried out in DCM with 100 mV s$^{-1}$ scan rate and data are reported vs. SCE in DCM.[11]

With the introduction of the complement 3, we observed a modest increase of the overall On for adduct 1•3 in DCM ($\Phi_{PL}$=25%) compared to free component 1 ($\Phi_{PL}$=20%) along with a color change from green ($\lambda_{PL}$=491, 518 nm) to deep blue ($\lambda_{PL}$=425, 494 nm) (CIE diagram of 1: x=0.23, y=0.56; 1•3: x=0.18, y=0.20.[25] Dual emission is observed, primarily ascribed to the components themselves, which is coupled with energy transfer from 3 to 1 as evidenced by the altered bi-exponential decay of $\tau_{PL}$=0.75 and 0.33 μs ($\lambda_{ex}$=378 nm and collected at $\lambda_{em}$=500 nm) in comparison to the emission decays of 1 and 3 (0.70 μs at $\lambda_{em}$=500 nm and 3.0 ns at $\lambda_{eb}$=400 nm, respectively). It is important to note that at 378 nm both components are directly photoexcited. We nevertheless ascribe the longer lifetime component to the direct photoexcitation of 1 (93% contribution), which is slightly elongated from that of free 1. We rationalize this small increase to be caused by an electronic perturbation of 1 imparted by the formation of host-guest complex 1•3. The shorter component can be linked to the excitation of 3 (7% contribution), and subsequent energy transfer to 1 in 1•3. The we see no evidence of the lifetime component of free 3.[26] We also collected the decay lifetime of 1•3 at $\lambda_{em}$=450 nm where both species exhibit photon emission. At this emission wavelength, the luminescence decay is dominated by the phosphorescence of 1 ($\tau_{PL}$=0.60 μs; 95% contribution) with a minor contribution from fluorescent 3 ($\tau_{PL}$=2.7 ns), demonstrating that the lifetime values are $\lambda_{em}$ dependent and attributed to a bimolecular system with coupled emission properties. This conclusion is further supported by comparison of the emission spectra of 1, 3 and 1•3 at equimolar concentrations (see FIG. 3b), where some emission quenching is evident of both components.

This phenomenon was also explored by performing a PL titration experiment of 1 titrated with 3 (with a background concentration of 1 to maintain a constant concentration) in CHCl$_3$/DMSO 98:2, modelling the same conditions as the UV-Vis binding study. Here, we see an increase of the emission intensity of 3 up to the equimolar mark with some quenching of 1 observed. Beyond a 1:1 concentration, we observe little increase (followed by some quenching) in emission intensity of 3 upon addition of up to 4 equivalents of 1, while only a partial quenching of 1 was observed. This experiment clearly illustrates that the emission properties of this host-guest pair are coupled. The energy transfer efficiency for 1•3 was also measured and calculated to be approximately 35% from the ratio between the corrected excitation spectrum of 1•3 (collected at 580 nm; beyond the emission window of 3) and the absorption spectrum of 1•3. (see FIGS. 3a)-c)).

The $\Phi_{PL}$ for the PMMA doped film prepared in 1:1 ratio of 1 and 3 to form 1•3 adduct is 23% (Table 1), with near quantitative quenching of 3. To probe the emission quenching of 3, a PMMA doped film containing a 1:1 ratio of 3 and the yellow emitting [Ir(ppy)$_2$(dtbubpy)]PF$_6$ (dtbubpy is 4,4'-di-tert-butyl-2,2'-bipyridine),[27] was prepared and analyzed. Here, no association by hydrogen bonding is present between both emitting species but, similarly to 1•3, we observed a complete emission quenching of 3. This demonstrates that one root cause of the quenching of 3 in both cases is due to aggregation-caused quenching in doped film. This is supported by an analogous experiment conducted in solution demonstrating that the emission of 3 was also quenched in solution but to a lesser extent, while $^1$H NMR analysis shows no discernable interactions with [Ir(ppy)$_2$(dtbubpy)]PF$_6$). The reduced loss of signal in the solution PL study also demonstrates that we are perturbing the [Ir(ppy)$_2$(dtbubpy)]PF$_6$ signal less than that of 1•3. This indicates that the intermolecular interactions afforded by the recognition motif in 1•3 are influencing the energy transfer (ET) in solution, the efficiency of which is a function of the distance between the donor and the acceptor units.[28] This does not rule out, however, quantitative ET from 3 to 1 in the solid-state since the quantum yields of 1•3 decrease slightly compared to solution data, while the opposite is true for 1. Given the highly conjugated nature of 3, its propensity to potentially act as an electron-transport/host material is also a likely contributor to this observation, and an avenue we are investigating further in the context of EL devices.

Figure 4:
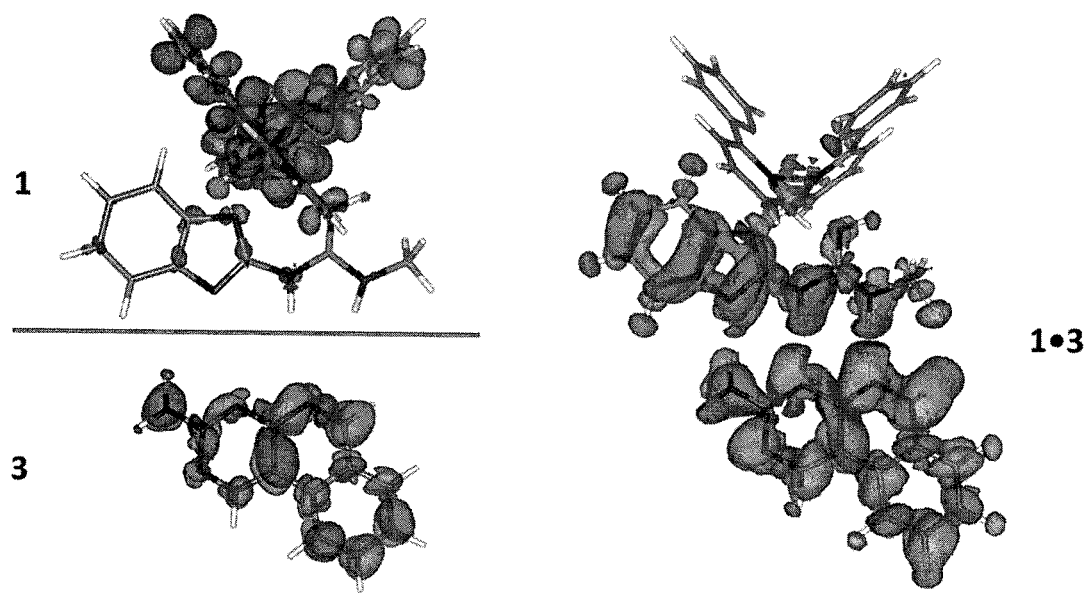
FIG. 4 are geometry optimized triplet spin-density difference distributions of 1, 3, and 1•3.

Electrochemical studies on complex 1, assembly 1•3, and compound 3 were performed using cyclic voltammetry (CV) and potentials of interest (vs. SCE)[11] reported in Table 1. Complex 1 exhibits a oxidation at $E_{pa}$=1.12 V, assigned to the Ir (III)/Ir (IV) redox couple[29] with contributions from the N^N$^-$ ligand. Upon introduction of 3 to a solution of 1, the potential of adduct 1•3 is anodically shifted to 1.17 V due to the formation of 1•3 H-bonded complex, which act to remove electron density from the benzimidazole portion of the N^N$^-$ ligand (the H-bond acceptor with the highest density of HOMO occupancy), thereby stabilizing the complex.[30] This analysis is further supported by the DFT calculations where the T$_1$ spin-density distributions show spin density shared across both components of 1•3 (FIG. 4). This intermolecular electronic communication between the heterodimer is further corroborated by DFT calculations where the frontier HOMO orbitals are situated largely on the Ir$^{III}$ centre and the N^N$^-$ ligand while the LUMO is entirely localized on 3. Thus, in both the ground and the excited states there is an electronic coupling between 1 and 3 in 1•3. Finally, the thermal stability was investigated by thermogravimetric analysis (TGA) under a nitrogen atmosphere. Complex 1 is thermally stable with a 5% weight-decomposition temperature $T_d$=288° C., which is desirable for possible implementation into OLED devices.

REFERENCES (1) a) Lu, K.-Y.; Chou, H.-H.; Hsieh, C.-H.; Yang, Y.-H. O.; Tsai, H.-R.; Tsai, H.-Y.; Hsu, L.-C.; Chen, C.-Y.; Chen, I.-C.; Cheng, C.-H. Wide-Range Color Tuning of Iridium Biscarbene Complexes from Blue to Red by Different N^N Ligands: An Alternative Route for Adjusting the Emission Colors. *Adv. Mater.* 2011, 23, 4933-4937. b) *Iridium (III) in Optoelectronic and Photonics Applications*, John Wiley & Sons, Ltd, 2017.

(2) a) Kando, A.; Hisamatsu, Y.; Ohwada, H.; Itoh, T.; Moromizato, S.; Kohno, M.; Aoki, S. Photochemical Properties of Red-Emitting Tris(cyclometalated) Iridium (III) Complexes Having Basic and Nitro Groups and Application to pH Sensing and Photoinduced Cell Death. *Inorg. Chem.* 2015, 54, 5342-5357. b) Jiang, J.; Zhang, C.; Lin, W.; Liu, Y.; Liu, S.; Xu, Y.; Zhao, Q.; Huang, W. Long-Lived Phosphorescent Iridium (III) Complexes Conjugated with Cationic Polyfluorenes for Heparin Sensing and Cellular Imaging. *Macromol. Rapid Commun.* 2015, 36, 640-646.

(3) Medina-Rodriguez, S.; Denisov, S. A.; Cudre, Y.; Male, L.; Marin-Suarez, M.; Fernandez-Gutierrez, A.; Fernandez-Sanchez, J. F.; Tron, A.; Jonusauskas, G.; McClenaghan, N. D.; Baranoff, E. High Performance Optical Oxygen Sensors Based on Iridium Complexes Exhibiting Interchromophore Energy Shuttling. *Analyst* 2016, 141, 3090-3097.

(4) McDaniel, N. D.; Bernhard, S. Solar Fuels: Thermodynamics, Candidates, Tactics, and Figures of Merit. *Dalt. Trans.* 2010, 39, 10021-10030.

(5) a) Martir, D. R.; Momblona, C.; Pertegás, A.; Cordes, D. B.; Slawin, A. M. Z.; Bolink, H. J.; Zysman-Colman, E. Chiral Iridium(III) Complexes in Light-Emitting Electrochemical Cells: Exploring the Impact of Stereochemistry on the Photophysical Properties and Device Performances. *ACS Appl. Mater. Interfaces* 2016, 8, 33907-33915. b) Henwood, A. F.; Bansal, A. K.; Cordes, D. B.; Slawin, A. M. Z.; Samuel, I. D. W.; Zysman-Colman, E. Solubilized Bright Blue-Emitting Iridium Complexes for Solution Processed OLEDs. *J. Mater. Chem. C* 2016, 4, 3726-3737. c) Duan, J. P.; Sun, P. P.; Cheng, C. H. New Iridium Complexes as Highly Efficient Orange-Red Emitters in Organic Light-Emitting Diodes. *Adv. Mater.* 2003, 15, 224-228.

(6) a) Skórka, Ł.; Filapek, M.; Zur, L.; Małecki, J. G.; Pisarski, W.; Olejnik, M.; Danikiewicz, W.; Krompiec, S. Highly Phosphorescent Cyclometalated Iridium(III) Complexes for Optoelectronic Applications: Fine Tuning of the Emission Wavelength through Ancillary Ligands. *J. Phys. Chem. C* 2016, 120, 7284-7294. b) Henwood, A. F.; Zysman-Colman, E. Lessons Learned in Tuning the Optoelectronic Properties of Phosphorescent Iridium (III)

Complexes. *Chem. Commun.* 2017, 53, 807-826. c) Chau, N.-Y.; Ho, P.-Y.; Ho, C.-L.; Ma, D.; Wong, W.-Y. Color-Tunable Thiazole-Based iridium (III) Complexes: Synthesis, Characterization and Their OLED Applications. *J. Organomet. Chem.* 2017, 829, 92-100.

(7) a) Xu, W.; Arieno, M.; Löw, H.; Huang, K.; Xie, X.; Cruchter, T.; Ma, Q.; Xi, J.; Huang, B.; Wiest, O.; Gong, L.; Meggers, E. Metal-Templated Design: Enantioselective Hydrogen-Bond-Driven Catalysis Requiring Only Parts-per-Million Catalyst Loading. *J. Am. Chem. Soc.* 2016, 138, 8774-8780. Skubi, K. L.; Kidd, J. B.; Jung, H.; Guzei, I. A.; Baik, M.-H.; Yoon, T. P. Enantioselective Excited-State Photoreactions Controlled by a Chiral Hydrogen-Bonding Iridium Sensitizer. *J. Am. Chem. Soc.* 2017, 139, 17186-17192.

(8) Crosby, G. A.; Demas, J. N. The Measurement of Photoluminescence Quantum Yields. *J. Phys. Chem.* 1971, 75, 991-1024.

(9) Melhuish, W. H., Quantum Efficiencies of Fluorescence of Organic Substances: Effect of Solvent and Concentration of the Fluorescent Solute. *J. Phys. Chem.* 1961, 65, 229-235.

(10) Greenham, N. C.; Samuel, I. D. W.; Hayes, G. R.; Phillips, R. T.; Kessener, Y. A. R. R.; Moratti, S. C.; Holmes, A. B.; Friend, R. H., Measurement of absolute photoluminescence quantum efficiencies in conjugated polymers. *Chem. Phys. Lett.*, 1995, 241, 89-96.

(11) Connelly, N. G.; Geiger, W. E. Chemical Redox Agents for Organometallic Chemistry. *Chem. Rev.* 1996, 96, 877-910.

(12) Sheldrick, G. M. SHELXT: Integrated Space-Group and Crystal-Structure Determination. *Acta Crystallogr. Sect. A* 2015, 71, 3-8.

(13) Sheldrick, G. M. Crystal Structure Refinement with SHELXL. *Acta Crystallogr. Sect. C, Struct. Chem.* 2015, 71 (Pt 1), 3-8.

(14) Dolomanov, O. V; Bourhis, L. J.; Gildea, R. J.; Howard, J. A. K.; Puschmann, H. OLEX2: A Complete Structure Solution, Refinement and Analysis Program. *J. Appl. Crystallogr.* 2009, 42, 339-341.

(15) www.supramolecular.org

(16) Thordarson, P. Determining Association Constants from Titration Experiments in Supramolecular Chemistry. *Chem. Soc. Rev.* 2011, 40, 1305-1323.

(17) Castro, A.; Martinez, A. Intramolecular Oxidative Cyclizations in Heteroarylthioureas: A Versatile Pathway to Bridgehead Heterocyclic Systems *J. Heterocycl. Chem.* 1999, 36, 991-995.

(18) Vig, R.; Mao, C.; Venkatachalam, T. K.; Tuel-Ahlgren, L.; Sudbeck, E. A.; Uckun, F. M. Rational Design and Synthesis of Phenethyl-5-Bromopyridyl Thiourea Derivatives as Potent Non-Nucleoside Inhibitors of HIV Reverse Transcriptase. *Bioorg. Med. Chem.* 1998, 6, 1789-1797.

(19) Ashworth, R. D. B.; Crowther, A. F. Synthetic Antimalarials; Some 2-Phenylureido- and 2-Phenylthioureido-4-Dialkylaminoalkylamino-6-Methylpyrimidines. *J. Chem. Soc.* 1948, 2, 581-586.

(20) Nonoyama, M. Benzo[h]quinolin-10-yl-N Iridium (III) Complexes *Bull. Chem. Soc. Jpn.* 1974, 47, 767-768.

(21) Pelphrey, P. M.; Popov, V. M.; Joska, T. M.; Beierlein, J. M.; Bolstad, E. S. D.; Fillingham, Y. A.; Wright, D. L.; Anderson, A. C. Highly Efficient Ligands for Dihydrofolate Reductase from Cryptosporidium Hominis and Toxoplasma Gondii Inspired by Structural Analysis. *J. Med. Chem.* 2007, 50, 940-950.

(22) Blight, B. A.; Camara-Campos, A.; Djurdjevic, S.; Kaller, M.; Leigh, D. A.; McMillan, F. M.; McNab, H.; Slawin, A. M. Z. AAA-DDD Triple Hydrogen Bond Complexes. *J. Am. Chem. Soc.* 2009, 131, 14116-14122.

(23) Rowland, R. S.; Taylor, R. Intermolecular Nonbonded Contact Distances in Organic Crystal Structures: Comparison with Distances Expected from van Der Waals Radii. *J. Phys. Chem.* 1996, 100, 7384-7391.

(24) Hsu, C.-W.; Longhi, E.; Sinn, S.; Hawes, C. S.; Young, D. C.; Kruger, P. E.; De Cola, L. Pyrazolo[4,3-h]quinoline Ligand-Based Iridium(III) Complexes for Electrochemiluminescence. *Chem. Asian J.* 2017, 12, 1649-1658.

(25) We acknowledge that the $\Phi_n$ value of 1·3 is ast the upper limit of the error for $\Phi_{PL}$ of 1; the $\Phi_{PL}$ for both systems were analyzed in triplicate to verify their validity.

(26) We see no evidence of the lifetime component of free 3, though this short lifetime component is likely masked by the biexponential decay and cannot be unequivocally deconvoluted from the data.

(27) Rota Martir, D.; Momblona, C.; Pertegás, A.; Cordes, D. B.; Slawin, A. M. Z.; Bolink, H. J.; Zysman-Colman, E. Chiral Iridium(III) Complexes in Light-Emitting Electrochemical Cells: Exploring the Impact of Stereochemistry on the Photophysical Properties and Device Performances. *ACS Appl. Mater. Interfaces* 2016, 8, 33907-33915.

(28) *Principles and Applications of Fluorescence Spectroscopy*, Jihad Rene Albani, John Wiley and Sons, 2008.

(29) Kim, J. Ii; Shin, I.-S.; Kim, H.; Lee, J.-K. Efficient Electrogenerated Chemiluminescence from Cyclometalated Iridium (III) Complexes. *J. Am. Chem. Soc.* 2005, 127, 1614-1615.

We claim:

1. A metal complex represented by the following general formula:

[structure diagrams of three metal complexes with benzimidazole-guanidine ligands]

X = 2 or 3
Y = N^N, N^C, or N^O chelates
R = Me, Et, Pr, Bu, or Ph
M = Al, Cd Pt, Pd, Rh, Ru, Ir, Ni, Cu, Zn, Co, Fe, Os, E, Eu, La, Tb, Dy, Sm, Nd, or Ce.

2. The metal complex of claim 1, wherein the metal complex is a transition metal complex.

3. The metal complex of claim 2, wherein the transition metal complex is an iridium (III) complex.

4. The metal complex of claim 3, wherein the iridium (III) complex has one of the following structures:

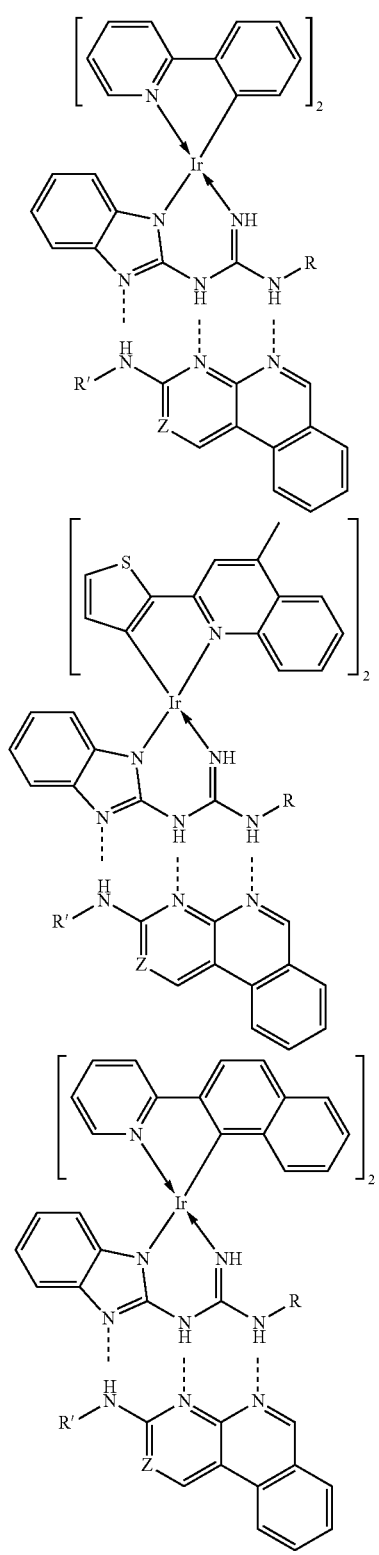

R = Me, Et, Pr, Bu, or Ph
R' = H, Me, Et, Pr, Bu, or Ph
Z = N or C.

5. A ligand having the following structure:

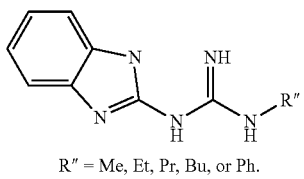

R" = Me, Et, Pr, Bu, or Ph.

6. A complimentary molecule having the following structure:

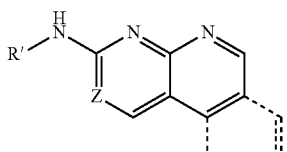

R' = H, Me, Et, Pr, Bu, or Ph
Z = N or C.

7. A method of altering photophysical properties in a metal complex comprising utilizing a ligand having the structure

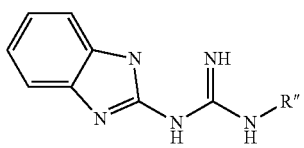

R" = Me, Et, Pr, Bu, or Ph and utilizing a complimentary molecule having the structure

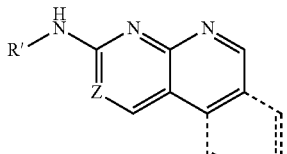

R' = H, Me, Et, Pr, Bu, or Ph
Z = N or C.

8. The method of claim 7, further comprising:
altering the energy gap between a conductive band and a valence band in the metal complex comprising, attaching the ligand having the structure

R" = Me, Et, Pr, Bu, or Ph to the metal complex, and controlling the interaction between the complimentary molecule having the structure

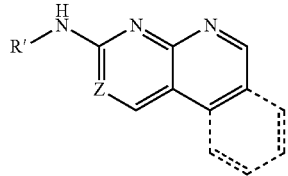

R' = H, Me, Et, Pr, Bu, or Ph
Z = N or C, and the ligand having the structure

R'' = Me, Et, Pr, Bu, or Ph, and the metal complex.

9. The metal complex of claim 2, wherein the transition metal complex is a cobalt (III) complex.

10. The metal complex of claim 2, wherein the transition metal complex is a rhodamine (III) complex.

11. The metal complex of claim 2, wherein the transition metal complex is a platinum (II) complex.

* * * * *